(12) United States Patent
Botschka et al.

(10) Patent No.: US 7,799,321 B2
(45) Date of Patent: Sep. 21, 2010

(54) COLOR COSMETIC COMPOSITIONS

(75) Inventors: Ellen S. Botschka, Riverdale, NJ (US); Barbara Krautsieder, Elmwood Park, NJ (US); Steven A. Orofino, Bronx, NY (US); Linda C. Foltis, Nutley, NJ (US)

(73) Assignee: ISP Investments Inc., Wilmington, DE (US)

( * ) Notice: Subject to any disclaimer, the term of this patent is extended or adjusted under 35 U.S.C. 154(b) by 291 days.

(21) Appl. No.: 11/395,605

(22) Filed: Mar. 31, 2006

(65) Prior Publication Data
US 2007/0231286 A1    Oct. 4, 2007

(51) Int. Cl.
*A61K 31/74* (2006.01)
(52) U.S. Cl. .................. 424/78.03; 510/475
(58) Field of Classification Search ........... None
See application file for complete search history.

(56) References Cited

U.S. PATENT DOCUMENTS 7,371,369 B2 *  5/2008  Shih ................ 424/78.02
2003/0118531 A1 *  6/2003  Kolodziej et al. ......... 424/63
2005/0226838 A1 * 10/2005  Krause et al. ............ 424/70.13
2006/0084586 A1 *  4/2006  Drzewinski et al. ....... 510/119
2007/0056900 A1 *  3/2007  Mathauer et al. ......... 210/500.1

FOREIGN PATENT DOCUMENTS

WO    WO 2005/032701    *  4/2005

* cited by examiner

Primary Examiner—Robert A Wax
Assistant Examiner—Bethany Barham
(74) Attorney, Agent, or Firm—William J. Davis; Thompson Hine LLP

(57) ABSTRACT

Color cosmetic compositions include a rheology modifier (thickener) and film-former copolymer which is a crosslinked, linear copolymer of poly(vinyl amide polymerizable carboxylic acid) e.g. poly(vinyl pyrrolidone-acrylic acid), which is compatible with iron oxides generally present in such compositions, e.g. gel and emulsion color cosmetic formulations such as gel eyelid enhancers, oil-in-water emulsion eyeliner and oil-in-water emulsion foundation products.

20 Claims, No Drawings

COLOR COSMETIC COMPOSITIONS

CROSS-REFERENCE TO RELATED U.S. PATENT APPLICATION

This application is related to pending U.S. patent application Ser. No. 10/964,948, filed Oct. 14, 2004, the disclosure of which is hereby incorporated by reference in its entirety.

BACKGROUND OF THE INVENTION

1. Field of the Invention

This invention relates to color cosmetic compositions, and, more particularly, to compatible gel and emulsion color compositions which include a crosslinked, linear poly(vinyl amide-polymerizable carboxylic acid) copolymer as rheology modifier (thickener) and film-former in such compositions.

2. Description of the Prior Art

J. Shih, in U.S. Pat. No. 5,015,708, described a process for making terpolymers of vinyl pyrrolidone, acrylic acid and lauryl methacrylate monomers by precipitation polymerization in an aliphatic hydrocarbon solvent.

Frenz, V. in WO 02/32975, Apr. 25, 2002, described absorbent materials made by grafting acrylic acid monomer onto polyvinyl pyrrolidone polymer in water in the presence of a crosslinking agent. The resultant crosslinked graft copolymer matrix contained 79.9-99.9% of acrylic acid.

However, most rheology modifiers, e.g. crosslinked acrylic acid, are incompatible with iron oxides present in color cosmetic compositions and do not provide film-forming properties for the compositions. Rheology modifiers known to be useful in conjunction with iron oxides, e.g., xanthan gum and cellulosics such as HPMC and HPC, tend to provide an unpleasant, unacceptable slimy feel.

SUMMARY OF THE INVENTION

We have discovered improved color cosmetic compositions which include a color ingredient e.g. an iron oxide, a copolymer which is a compatible rheology modifier and film-former, and which provide an aesthetically pleasing application and end feel.

In another embodiment of this invention, there is provided a gel and emulsion color cosmetic formulations in which a crosslinked, linear poly(vinyl amide-polymerizable carboxylic acid) copolymer is present as thickener and film-former and is compatible with iron oxides in such formulations.

A specific object of this invention is to use a crosslinked, linear copolymer of poly(vinyl pyrrolidone-acrylic acid) as rheology modifier and film-former in color cosmetic compositions containing iron oxides in compatible formulations such as gel and oil-in-water emulsions, e.g. gel eyelid enhancers, oil-in-water emulsion eyeliner, and oil-in-water emulsion foundation products.

DETAILED DESCRIPTION OF THE INVENTION

What is described herein is the use of a rheology modifier/personal care resin which is a crosslinked, linear poly(vinyl amide/polymerizable carboxylic acid) copolymer in color cosmetic compositions. The color cosmetic composition includes a color ingredient, e.g. iron oxide, and a compatible crosslinked, linear copolymer of poly(vinylamide-polymerizable carboxylic acid) as rheology modifier and film-former, e.g. in compositions which are gels or emulsions, e.g. oil-in-water or water-in-oil emulsions.

Representative color cosmetic composition include an eyelid enhancer, an eyeliner and foundation compositions.

Suitably the color cosmetic composition of the invention includes about 0.1-20 wt. % of the defined copolymer, preferably 0.2 to 10 wt. %.

Preferably, the copolymer is a crosslinked, linear poly(vinyl pyrrolidone-acrylic acid) copolymer, most preferably comprising about 10-90 wt. % of vinyl pyrrolidone and about 10-90 wt. % of acrylic acid.

Suitable vinyl amides include vinyl pyrrolidone, vinyl caprolactam, N-vinyl formamide, N-vinylacetamide, N-vinyl-N-methylacetamide and mixtures thereof, preferably vinyl pyrrolidone.

Suitable polymerizable carboxylic acids include (meth) acrylic acid, crotonic acid, itaconic acid, maleic acid and mixtures thereof, preferably acrylic acid.

Suitable crosslinkers have at least two free radical polymerizable groups in the molecule, e.g. pentaerythritol triallylether, pentaerythritol triacrylate, pentaerythritol tetraacrylate or methylene bisacrylamide.

The composition of the rheology modifier/personal care resin of the present invention includes a vinyl amide, in an amount of by weight, 1-99% of the composition, a polymerizable carboxylic acid in an amount of 1-99% of the composition, and a crosslinker in an amount of 0.2-3%, based on total weight of monomers.

Preferably, the vinyl amide monomer is present in an amount of 25-80%, the polymerizable carboxylic acid in an amount of 20-80%, and the crosslinker 0.4-2%, based on total weight of monomers.

Optionally, the rheology modifier/personal care resin may include one or more additional monomers, e.g. lauryl(meth) acrylate, stearyl(meth)acrylate, alkyl(meth)acrylamide or alkyl(meth)acrylate. The alkyl group can be $C_1$ to $C_{30}$ or polyethylene oxide.

The rheology modifier/personal care resin is made by precipitation polymerizing, by wt., 5-50%, preferably 10-25%, of a mixture of a vinyl amide, a polymerizable carboxylic acid and a crosslinker, in the presence of 50-95%, preferably 75-90%, of a non-polar, removable organic solvent, and 0.1-5%, preferably 0.5-2%, of a free radical initiator, based on total weight of monomers.

The rheology modifier copolymer resin of the invention, suitably is present in the color cosmetic composition in an amount of 0.1-20% by wt., preferably 0.2-10%, and most preferably 0.3-5%, of the composition.

The color ingredient can be dispersed by conventional mixing techniques preferably in the water phase after the rheology modifier has been dispersed in the water phase. Suitable color ingredients include pigments, such as iron oxides, titanium dioxides, organic pigments, the Lakes, ultramarines, and the like. Suitable iron oxides include red iron oxides, yellow iron oxides, black iron oxides and known iron oxides.

Preferred cosmetic colorants (approved for use in the United States) include Ext. D & C Yellow No. 2, D & C Red No. 36, FD & C Red No. 4, D & C Orange No. 4, D & C Red No. 31, D & C Red No. 6, D & C Red No. 7, D & C Red No. 34, FD & C Yellow No. 6, FD & C Red No. 40, D & C Red No. 33, FD & C Yellow No. 5, D & C Brown No. 1, D & C Red No. 17, FD & C Green No. 3, D & C Blue No. 4, FD & C Blue No. 1, D & C Yellow No. 8, D & C Yellow No. 7, D & C Orange No. 5, D & C Red No. 22, D & C Red No. 21, D & C Red No. 28, D & C Red No. 27, D & C Orange No. 11, D & C Orange No. 10, D & C Yellow No. 11, D & C Yellow No. 10, D & C Green No. 8, D & C Violet No. 2, Ext. D & C Violet No. 2, D & C Green No. 6, D & C Green No. 5, D & C Red No. 30, Annatto, Beta-Carotene, Guanine, Carmine, Henna, Chlorphyllin-Copper, Complex Aluminum Powder, Ultramarines, Mica, Bismuth Oxychloride, Chromium Oxide Greens, Chromium Hydroxide, Green, Bronze Powder, Copper Powder, Iron Oxides, Ferric Ferrocyanide, Ferric Ammonium, Ferrocyanide, Manganese Violet, Silver, Titanium Dioxide, Zinc Oxide, Bismuth Citrate, Caramel, Dihydroxyacetone, Disodium EDTA-Copper, Gualazulene, LeadAcetate, and Pyrophyllite.

Typically color cosmetic compositions of the invention which include the invention resin have an advantageously high viscosity of about 30,000 to 100,000 cps, preferably 40,000 to 80,000 cps, at a pH of about 5 to 9.

The crosslinked linear copolymer used herein is sold by International Specialty Products as Ultrathix™ P-100.

The scope of the invention is illustrated by the following Table.

The process of making the crosslinked linear copolymer of the invention is shown in Examples 1-15 which follow.

EXAMPLE 1

Crosslinked, Linear Poly(N-Vinyl Pyrrolidone) (VP)/Acrylic Acid (AA) Copolymer Crosslinked with Pentaerythritol Triallyl Ether (PETE)

Into a 1-liter, four-necked glass kettle, equipped with two feeding pumps, an anchor agitator, a thermocouple and a condenser, 500 g of heptane as solvent was charged and agitated at 200 rpm while being purged with nitrogen throughout the process. The solvent then was heated to 65° C. with an oil bath and held there for 30 minutes. Feeding Solution I was prepared by mixing 50 g of N-vinylpyrrolidone (VP) and 1.0 g of pentaerythritol triallylether (PETE). Feed-

TABLE

RHEOLOGY MODIFIER/COLOR COSMETIC RESIN OF THE INVENTION

| Monomer | Example | Suitable Compositional Range | Preferred Compositional Range |
|---|---|---|---|
| Vinyl amide | Vinyl pyrrolidone, Vinyl caprolactam, N-vinyl-formamide, N-vinyl acetamide, N-vinyl-N-methyl acetamide | 1-99% | 20-80% |
| Polymerizable carboxylic acid | (Meth)acrylic acid, crotonic acid, itaconic acid, maleic acid | 1-99% | 20-80% |
| Crosslinker, more than two free radical polymerizable groups in the molecule | Pentaerythritol triallylether, methylene bisacrylamide, pentaerythritol triacrylate, pentaerythritol tetraacrylate | 0.2-3% based on total weight of monomers | 0.4-2 |
| Optional monomers | Lauryl (meth)acrylate, stearyl (meth)acrylate, alkyl (meth)acrylamide, alkyl(meth)acrylate | | |
| Free radical initiator, e.g. peroxide, perester, percarbonate, Vazo | t-Butylperoxy pivalate, 2,2'-azobis(2-methylbutanenitrile) | 0.1-5%, based on total monomer weight | 0.5-2% |
| Volatile non-polar organic solvent or mixed solvents | Heptane, benzene, isopropyl acetate, cyclohexane | 95-50% (solvent) 5-50% (polymer) | 85-75% 15-25% |

| Process Conditions | Suitable Range | Preferred Range |
|---|---|---|
| Polymerization temperature | 40° C.-150° C. | 55° C.-100° C. |
| Monomer feeding time, hrs (2 feeding lines) | 0-10 | 3-5 |

The process of making the rheology modifier/color cosmetic resin of the present invention is suitably carried out in a non-polar solvent, e.g. heptane, benzene, isopropyl acetate or cyclohexane, which can be removed easily after the polymerization, in the presence of a free radical initiator, at a polymerization temperature of 40°-150° C., preferably 55°-100° C., at monomer feeding times in 2 feeding lines of 0-10 hrs, preferably 3-5 hrs. The reactants are monomers and crosslinker. The product is a crosslinked, linear copolymer of a vinyl amide, e.g. vinyl pyrrolidone, and a polymerizable carboxylic acid, e.g. acrylic acid, which is crosslinked with a suitable crosslinking agent e.g. pentaerythritol triallyl ether in the form of a powder.

Aqueous solutions of the resin of the invention also have the advantageous property of a high yield stress, generally 10 to 100,000, and preferably 100 to 10,000, in dynes/cm$^2$.

ing Solution II was prepared by weighing 50 g of acrylic acid (AA) into a bottle. 200 microliter of Luperox® 11M75 as initiator was charged into the kettle. Then Feeding Solutions I and II were simultaneously pumped into the kettle over a period of 4 hours at a constant feeding rate. The resulting solution then was held at 65° C. for 1 hour and the reaction temperature was raised to 90° C. Then an additional 100 microliter of Luperox® 11M75 was added every two hours for 4 times and the reactor was held at 90° C. for two additional hours after the last dose of Luperox® 11M75 was charged. The contents then were cooled and discharged. The solvent was removed at an oven temperature of 100° C. The resultant resin powder was further dried in a vacuum oven at 100° C. The product was a crosslinked, linear copolymer of VP and AA crosslinked with PETE in a wt. ratio of 50/50/1.

EXAMPLES 2-15

| Example | VP (g) | AA (g) | PETE (g) |
| --- | --- | --- | --- |
| 2 | 75 | 25 | 0.5 |
| 3 | 50 | 50 | 0.5 |
| 4 | 25 | 75 | 0.5 |
| 5 | 75 | 25 | 1.0 |
| 6 | 50 | 50 | 2.0 |
| 7 | 25 | 75 | 1.0 |
| 8 | 75 | 25 | 1.5 |
| 9 | 50 | 50 | 1.5 |
| 10 | 25 | 75 | 1.5 |

EXAMPLE 11

Crosslinked, Linear Poly(N-Vinyl Caprolactam) (VCL)/Acrylic Acid) Copolymer Crosslinked with Pentaerythritol Triallyl Ether Into a 1-liter, four-necked glass kettle, equipped with an anchor agitator, a thermocouple and a condenser, 500 g of heptane as solvent was charged and agitated at 200 rpm while being purged with nitrogen throughout the process. The solvent then was heated to 65° C. with an oil bath and held there for 30 minutes. Feeding Solution I was prepared by mixing 50 g of N-vinylcaprolactam (VCL) and 1.5 g of pentaerythritol triallylether (PETE). Feeding solution II was prepared by weighing 50 g of acrylic acid (AA) into a bottle. Then 200 microliter of t-butyl peroxypivalate initiator was charged into the kettle. The Feeding Solution I and Feeding Solution II were simultaneously charged into the kettle over 4 hours at a constant feeding rate. The solution was held at 65° C. for 1 hour and the temperature was raised to 90° C. Then an additional 200 microliter of t-butyl peroxypivalate was added every two hours for 4 times and the reactor was held at 90° C. for two additional hours after the last dose of t-butyl peroxypivalate was charged. The contents then were cooled and discharged. The solvent was removed at an oven temperature of 100° C. The resultant resin powder was further dried in a vacuum oven at 100° C. The product was a crosslinked, linear copolymer of VCL and AA crosslinked with PETE in a wt. ratio of 50/50/1.5.

EXAMPLE 11A

Crosslinked, Linear Poly(N-Vinyl/Pyrrolidone)/Acrylic Acid/Stearyl Methacrylate (SM) Terpolymer Crosslinked with Pentaerythritol Triallyl Ether Into a 1-liter, four-necked glass kettle, equipped with two feeding pumps, an anchor agitator, a thermocouple and a condenser, 500 g of heptane as solvent was charged and agitated at 200 rpm while being purged with nitrogen throughout the process. The solvent then was heated to 65° C. with an oil bath and held there for 30 minutes. Feeding Solution I was prepared by mixing 60 g of N-vinylpyrrolidone (VP), 15 g of stearyl methacrylate (SM) and 1.0 g of pentaerythritol triallylether (PETE). Feeding Solution II was prepared by weighing 25 g of acrylic acid (AA) into a bottle. 200 microliter of Luperox® 11M75 as initiator was charged into the kettle. Then Feeding Solutions I and II were simultaneously pumped into the kettle over a period of 4 hours at a constant feeding rate. The resulting solution then was held at 65° C. for 1 hour and the reaction temperature was raised to 90° C. Then an additional 100 microliter of Luperox® 11M75 was added every two hours for 4 times and the reactor was held at 90° C. for two additional hours after the last dose of Luperox® 11M75 was charged. The contents then were cooled and discharged. The solvent was removed at an oven temperature of 100° C. The resultant resin powder was further dried in a vacuum oven at 100° C. The product was a crosslinked, linear terpolymer of VP, AA and SM crosslinked with PETE in a wt. ratio of 600/25/15/1.

EXAMPLES 12-14

| Example | VCL (g) | AA (g) | PETE (g) |
| --- | --- | --- | --- |
| 12 | 75 | 25 | 1.5 |
| 13 | 25 | 75 | 1.5 |
| 14 | 50 | 50 | 2.0 |

EXAMPLE 15

Crosslinked, Linear Poly(N-Vinyl Pyrrolidone)/Methacrylic Acid (MAA) Copolymer Crosslinked with Pentaerythritol Triallyl Ether Into a 1-liter, four-necked glass kettle, equipped with two feeding pumps, an anchor agitator, a thermocouple and a condenser, 600 g of heptane as solvent is charged and agitated at 300 rpm while being purged with nitrogen throughout the process. The solvent then is heated to 70° C. with an oil bath and held there for 30 minutes. Feeding Solution I is prepared by mixing 50 g of N-vinylpyrrolidone (VP) and 1.0 g of pentaerythritol triallylether (PETE). Feeding solution II is prepared by weighing 50 g of methacrylic acid (MAA) into a bottle. Then 300 microliter of t-butyl peroxypivalate initiator is charged into the kettle.

The Feeding Solution I and Feeding Solution II are simultaneously pumped into the kettle over 5 hours at a constant feeding rate. The solution is held at 70° C. for 1 hour and the solution is transferred to stainless high pressure reactor. Then an additional 0.5 g of di-t-butylperoxide is added. The temperature of the reactor is raised to 130° C. and held for 10 hours. The contents then are cooled and discharged. The solvent is removed at an oven temperature of 100° C. The resultant resin powder is further dried in a vacuum oven at 100° C. The product is a crosslinked, linear copolymer of VP and MM crosslinked with PETE in a wt. ratio of 50/50/1.

Examples 16-18 below are illustrative of color cosmetic compositions of the invention which include Ultrathix P-100 as rheology modifier-film former therein.

EXAMPLE 16

| Eyelid Enhancer Gel | | | |
| --- | --- | --- | --- |
| Phase | Ingredient | % w/w | Supplier |
| A | Deionized water | 83.29 | |
| | Ultrathix P-100 (Ex. 1) | 1.00 | ISP |
| B | TEA 99% | 1.04 | |
| | Deionized water | 5.00 | |
| C | Liquid Germall Plus | 0.50 | ISP |

-continued

| Eyelid Enhancer Gel | | | |
|---|---|---|---|
| Phase | Ingredient | % w/w | Supplier |
| D | Aquaflex XL-30 | 6.67 | ISP |
| E | Timica Gold Sparkle | 2.00 | Engelhard |
|  | Timica Nu-Antique Bronze | 0.50 | Engelhard |
|  |  | 100.00 |  |

Procedure:
1. Charge vessel with water. Disperse Ultrathix P-100 into the water with vigorous agitation.
2. Add pre-mixed Phase B to batch using moderate sweep agitation. Batch will thicken. Mix until uniform.
3. Add Phase C to batch. Mix until uniform.
4. Add Phase D. Mix until uniform.
5. Add Phase E to batch slowly, avoid aerating batch. Mix until uniform.

Properties:
pH=7.47
Visc.=68,800 cps (TC @ 5 RPM)
Forms stable color films which dry rapidly.

EXAMPLE 17

| O/W Emulsion Eyeliner | | | |
|---|---|---|---|
| Phase | Ingredient | % w/w | Supplier |
| A | Deionized water | 57.68 |  |
|  | Disodium EDTA | 0.10 |  |
|  | Ultrathix P-100 (Ex. 1) | 1.00 |  |
|  | TEA 99% | 0.06 |  |
| B | C33-134 Iron Oxide Black | 10.00 | Sun Chemical |
| C | TEA 99% | 0.98 |  |
| D | White Beeswax | 5.00 | Frank B. Ross |
|  | Carnauba Wax #1 Yellow Bleached | 3.30 | Frank B. Ross |
|  | Cerasynt 840 | 2.00 | ISP |
|  | Cerasynt 945 | 3.00 | ISP |
| E | Aquaflex XL-30 | 16.68 | ISP |
| F | Germall Plus | 0.20 | ISP |
|  |  | 100.00 |  |

Procedure:
1. Heat Phase A water to 85 C, add disodium EDTA; mix until uniform.
2. Sprinkle Ultrathix P-100 into batch using slow homo-mixing; add Phase A aliquot of TEA, batch will thicken slightly.
3. Add pre-pulverized Phase B to batch using homo-mixing. Mix until uniform.
4. Add Phase C to batch; batch will thicken; mix until uniform.
5. Heat Phase D to 87° C. Add to main batch and mix until uniform.
6. Switch to sweep-mixing; begin slow-cooling the batch to 55° C.
7. Add Phase E to batch; mix until uniform.
8. Cool batch to 450 C. Add Phase F and mix until uniform.
9. Continue sweep-mixing and slow-cooling to 30° C. Fill containers.

Properties:
pH=7.53
Visc.=76,000 cps (TC @ 5 RPM)
Forms stable film, does not rub-off easily.

EXAMPLE 18

| O/W Emulsion | | | |
|---|---|---|---|
| Phase | Ingredient | % w/w | Supplier |
| A | Deionized water | 51.45 |  |
|  | Disodium EDTA | 0.10 |  |
|  | TEA 99% | 0.05 |  |
|  | Ultrathix P-100 (Ex. 1) | 0.40 | ISP |
|  | Butylene Glycol | 4.00 |  |
| B | TEA 99% | 0.25 |  |
| C | SB 700 Silica Beads | 1.00 | U.S. Cosmetics |
|  | BTD-401 ITT treated Titanium Dioxide | 6.78 | Kobo |
|  | BYO-12 ITT treated Yellow Iron Oxide | 0.87 | Kobo |
|  | BRO-12 ITT treated Red Iron Oxide | 0.33 | Kobo |
|  | BBO-12 ITT treated Black Iron Oxide | 0.20 | Kobo |
|  | O-13 ITT treated Sericite | 1.82 | Kobo |
| D | Orchid Complex OS | 4.00 | ISP |
|  | Prolipid 141 | 5.00 | ISP |
|  | Ceraphyl 140 | 1.50 | ISP |
|  | Ceraphyl 494 | 0.75 | ISP |
|  | Escalol 557 | 7.00 | ISP |
|  | Escatol 567 | 2.00 | ISP |
|  | Escalol 587 | 3.00 | ISP |
|  | Si-Tec DM 350 | 1.00 | ISP |
| E | Allianz OPT | 1.00 | ISP |
| F | Si-Tec CM 040 | 3.00 | ISP |
| G | Germall Plus | 0.50 | ISP |
| H | Si-Tec DM 1 Plus | 4.00 | ISP |
|  |  | 100.00 |  |

Procedure:
1. Heat Phase A water to 75° C.; add disodium EDTA and Phase A aliquot of TEA 99%; mix until uniform.
2. Sprinkle Ultrathix P-100 into batch using slow homo-mixing, batch will thicken slightly. When uniform, add butylene glycol, mix until uniform.
3. Add Phase B to batch; mix until uniform; batch will thicken.
4. Preblend Phase C (pulverize). Add Phase C to Phase D at 75° C. using homo-mixer.
5. Add Phase C and D (70-75° C.) to Phase A and B (75° C.) using homo-mixing.
6. Homogenize for 10 minutes.
7. Add Phase E with homo-mixing; mix until uniform.
8. Cool to 55° C., w/slow homo-mixing; add F and G (pre-mixed). Mix until uniform.
9. Switch to sweep-mixing; cool batch to R.T. with sweep-mixing.
10. Add Phase H to batch at RT; mix until uniform.

Properties:
pH=6.0
Visc.=78,000 cps (TC @ 5 RPM)
A shiny emulsion which applies easy and forms a uniform film on skin.

What is claimed is:

1. A color cosmetic composition comprising a color ingredient and a compatible crosslinked, linear copolymer of poly(vinylamide-polymerizable carboxylic acid) as rheology modifier and film-former wherein said color ingredient comprises iron oxide and said crosslinked, linear copolymer has a composition of 1-99% of a vinyl amide polymer selected from the group consisting of vinyl pyrrolidone, vinyl caprolactam, N-vinyl formamide, N-vinyl-acetamide, N-vinyl-N-methylacetamide and mixtures thereof, and 1-99% of a polymerizable carboxylic acid monomer selected from the group consisting of (meth)acrylic acid, crotonic acid, itaconic acid, maleic acid and mixtures thereof, and a crosslinker in an amount of 0.2-3% based on weight of total monomers.

2. A color cosmetic composition according to claim 1 which is a gel.

3. A color cosmetic composition according to claim 1 which is an emulsion.

4. A color cosmetic composition according to claim 3 which is an oil-in-water emulsion.

5. A color cosmetic composition according to claim 1 which is an eyelid enhancer composition.

6. A color cosmetic composition according to claim 1 which is an eyeliner composition.

7. A color cosmetic composition according to claim 1 which is a foundation composition.

8. A color cosmetic composition according to claim 1 which includes 0.1-20 wt. % of said copolymer.

9. A color cosmetic composition according to claim 8 which includes 0.2-10 wt. % of said copolymer.

10. A color cosmetic composition according to claim 1 in which said copolymer is a crosslinked, linear poly(vinyl pyrrolidone-acrylic acid) copolymer.

11. A color cosmetic composition according to claim 10 in which said copolymer comprises 10-90 wt. % of vinyl pyrrolidone and 10-90 wt. % of acrylic acid.

12. A color cosmetic composition according to claim 1 wherein said cosmetic composition has a viscosity of about 30,000 to 100,000 cps. at a pH of about 5 to 9.

13. A color cosmetic composition according to claim 1 wherein said cosmetic composition is selected from the group consisting of a foundation, an eyelid enhancer composition, and an eyeliner composition.

14. A color cosmetic composition according to claim 1 wherein said iron oxide is selected from the group consisting of red iron oxides, yellow iron oxides, black iron oxides and mixtures thereof.

15. A color cosmetic composition according to claim 1 wherein said copolymer comprises a crosslinked, linear poly(vinyl pyrrolidone-acrylic acid) copolymer and said crosslinker is selected from the group consisting of pentaerythritol triallylether, pentaerythritol triacrylate, pentaerythritol tetraacrylate and methylene bisacrylamide.

16. A color cosmetic composition according to claim 15 wherein said copolymer comprises 10-90 wt. % of vinyl pyrrolidone and 10-90 wt. % of acrylic acid.

17. A color cosmetic composition comprising a color ingredient and a rheology modifier and film-former compatible with said color ingredients wherein said rheology modifier and film-former comprises a crosslinked, linear copolymer of poly(vinylamide-polymerizable carboxylic acid) containing a crosslinker selected from the group consisting of pentaerythritol triallylether, pentaerythritol triacrylate, pentaerythritol tetraacrylate and methylene bisacrylamide and said color ingredient comprises an iron oxide, wherein said color cosmetic composition is in the form of a gel or an emulsion and is an eyelid enhancer composition, an eyeliner composition or a foundation composition.

18. A color cosmetic composition according to claim 11 wherein said cosmetic composition has a viscosity of about 30,000 to 100,000 cps at a pH of about 5 to 9.

19. A color cosmetic composition according to claim 1 wherein the crosslinker has at least two free radical polymerizable groups in the molecule.

20. A color cosmetic composition according to claim 19 wherein the vinyl amide monomer is present in an amount of 25-80%, the polymerizable carboxylic acid is present in an amount of 20-80% and the crosslinker is present in an amount of 0.4-2% based on total weight of monomers.

* * * * *